United States Patent [19]
Grifantini et al.

[11] Patent Number: 5,834,258
[45] Date of Patent: Nov. 10, 1998

[54] PROCESS FOR THE PREPARATION OF D-α-AMINO ACIDS

[75] Inventors: Renata Grifantini, Milano; Giuliano Galli, S. Donato Milanese; Giovanna Carpani, Sergnano; Guido Grandi, Segrate, all of Italy

[73] Assignee: Eniricerche S.p.A., Milan, Italy

[21] Appl. No.: 744,829

[22] Filed: Nov. 6, 1996

[30] Foreign Application Priority Data

Nov. 23, 1995 [IT] Italy ................................. MI95A2432

[51] Int. Cl.$^6$ .............................. C12P 13/04; C12N 1/20; C12N 15/00
[52] U.S. Cl. ............... 435/106; 435/252.31; 435/252.33; 435/320.1; 935/22
[58] Field of Search .................... 435/106, 280, 435/320.1, 252.3, 252.31, 252.33; 935/22

[56] References Cited

FOREIGN PATENT DOCUMENTS 94005477  1/1994  WIPO .

OTHER PUBLICATIONS

Kim et al. (1995) Optimization of the enzymatic synthesis of D–p–hydroxyphenylglycine from DL–5–substituted hydantoin using D–hydantoinase and N–carbomoylase, Enzyme and Microbial Technology 17: 63–67, Jan. 1995.

Deepa et al. (1993) Enzymatic production and isolation of D–amino acids from the corresponding 5–substituted hydantoins. Process Biochemistry 28: 447–452, Apr. 1993.

*Primary Examiner*—Robert A. Wax
*Assistant Examiner*—Einar Stole
*Attorney, Agent, or Firm*—Oblon. Spivak, McClelland, Maier & Neustadt, P.C.

[57] ABSTRACT

In an improved process for the preparation of D-α-amino acids by the stereoselective conversion of racemic mixtures of 5-substituted hydantoins with an enzymatic system produced by a microorganism, the improvement consists in the fact that a microorganism is used which is transformed with the plasmid pSM700 cultivated at a temperature of between 20° C. and 28° C. The use of this microorganism allows an improvement in the expression of the enzymatic system and an increase in the conversion rate of the racemic hydantoin to D-α-amino acid.

16 Claims, 4 Drawing Sheets

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( i i ) MOLECULE TYPE: other nucleic acid ( x i ) SEQUENCE DESCRIPTION: SEQ ID NO:1:

AAGGAGGAAA AATAT                      1 5

-continued (2) INFORMATION FOR SEQ ID NO:2:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

AGCTTAAGGA GGAAAAATAT ATGGATATCC TGCA        34

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:3:

ATTCCTCCTT TTTATATACC TATAGG        26

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

AAAGGAGGAA TTCTTATG        18

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

AAGGAGGAAA AATATATG        18

PROCESS FOR THE PREPARATION OF D-α-AMINO ACIDS

The present invention relates to an improved process for the preparation of D-α-amino acids by the stereoselective conversion of racemic mixtures of 5-substituted hydantoins with an enzymatic system produced by a microorganism wherein the improvement consists in the fact that a microorganism is used transformed with the plasmid pSM700 cultivated at a temperature of between 20° C. and 28° C.

The term enzymatic system refers to a system consisting of D-hydantoinase and D-N-carbamoylase enzymes.

D-α-amino acids are extremely valuable compounds useful in the preparation of pharmacologically active substances (for example, D-phenylglycine and D-parahydroxyhphenylglycine are used in the synthesis of penicillin and semisynthetic cephalosporins, pesticides (D-valine for the synthesis of the insecticide fluvanilate). or sweeteners (D-alanine).

Processes are known in the art for the preparation of D-α-amino acids by the chemical and/or enzymatic hydrolysis of the corresponding 5-substituted hydantoins.

For example the patent FR 2.310.986 describes a process in which 5-substituted hydantoins are chemically hydrolyzed in racemic mixtures of D,L-amino acids from which the isomer of interest is subsequently separated.

Patent FR 2.317.357 discloses a process in which racemic mixtures of 5-subsituted hydantoins are subjected to enzymatic hydrolysis and the products of this transformation (N-carbamoyl-D-α-amino acids) are chemically oxidated into the corresponding D-α-amino acids.

These known processes have disadvantages deriving from the complex processes for the resolution and purification of the D-α-amino acids. As a result these processes are not economically interesting from an industrial point of view.

To overcome these inconveniences processes have been proposed in the art wherein D-α-amino acids are obtained directly from 5-substituted hydantoins by hydrolysis with enzymatic systems produced by microorganisms such as Pseudomonas, Moraxella, Agrobacterium, Hansenula, Arthrobacter (EP-199.943, EP-309.310, U.S. Pat. No. 4,312,948, FR 2456728).

The preparation of these enzymatic systems requires, however, the use of efficient inducers capable of stimulating the production of these enzymes on the part of the microorganisms. It is known, in fact, that the expression level of the enzymes D-hydantoinase and D-N-carbamoylase is constitutively very low (Syldatk et al. (1990), "Advances in Biochem. Engineering/Biotechnology (Fiechter, A. Ed.), 41, pages 29–75, Springer-Verlag, Berlin).

The use of inducers causes however a series of disadvantages among which an increase in the production costs and a certain variability in the production yields of the enzymes. In addition, the expression level which can be obtained in most of the microorganisms following induction is inadequate for their economic use in industrial processes (Syldatk et al. (1987), Biotechnol. lett., 9: 25–30; Yokozeki et al. (1987) Agric. Biol. Chem., 51, 715–722).

The genes which encode the D-hydantoinase and D-Ncarbamoylase enzymes have recently been sequenced and singly cloned (U.S. Pat. No. 4,912,044 and EP-515.698).

More specifically, the patent U.S. Pat. No. 4,912,044 describes the preparation of D-hydantoinase by the fermentation of a microorganism transformed with a hybrid vector containing the hydantoinase gene whose expression is induced by temperature variation. The enzyme thus obtained is used for the production of D-N-α-carbamoyl deriving from 5-substituted hydantoins.

Patent application EP-515.698 describes the preparation of D-N-α-carbamoylase by the fermentation of a microorganism transformed with a plasmid comprising the carbamoylase gene whose expression is chemically induced with IPTG. The enzyme thus obtained is used for the production of D-α-amino acids from N-carbamoyl derivatives.

As industrial interest lies in the conversion of racemic hydantoins to D-α-amino acids, the fact that the two enzymes are expressed in different strains involves the use of both and therefore the development of a procedure starting from two distinct fermentative processes. This leads to an increase in the production costs and reduces the conversion kinetics.

To overcome these drawbacks, a process for the conversion of 5-substituted hydantoins into D-α-amino acids has been proposed in the art which uses a microorganism transformed with a plasmid containing the hydantoinase and carbamoylase genes arranged in tandem and regulated by a single promoter. The two genes are constitutively expressed (without inducers) in a single cellular compartment (Italian patent application MI94A00726).

It has now been found that it is possible to improve the process described above by using a microorganism of the present invention, obtained by transformation with the plasmid pSM700 and fermentation at a temperature of between 20° and 28° C.

Operating in the presence of this microorganism it is possible, in fact, to improve both the expression of the enzymatic system and the conversion rate of racemic mixtures of 5-substituted hydantoins into the corresponding D-α-amino acids.

In accordance with this the present invention relates to a process for the production of D-α-amino acids by the stereoselective conversion of racemic mixtures of 5-substituted hydantoins with an enzymatic system produced by a microorganism, characterized in that said microorganism is obtained by:

(a) construction of the plasmid pSM700 comprising the carbamoylase-hydantoinase operon under the control of a constitutive promoter and where the region comprising the SD upstream of the hydantoinase gene has the sequence AAGGAGGAAA AATAT;

(b) transformation of a microorganism with the plasmid pSM700;

(c) fermentation of the transformed microorganism in an aqueous medium containing assimilable sources of carbon and nitrogen, cations, anions and, optionally, vitamins, under aerobic conditions, at a temperature of between 20° and 28° C.

BRIEF DESCRIPTION OF DRAWINGS

A brief description of the figures follows to provide a better illustration of the present invention.

Figure 6:
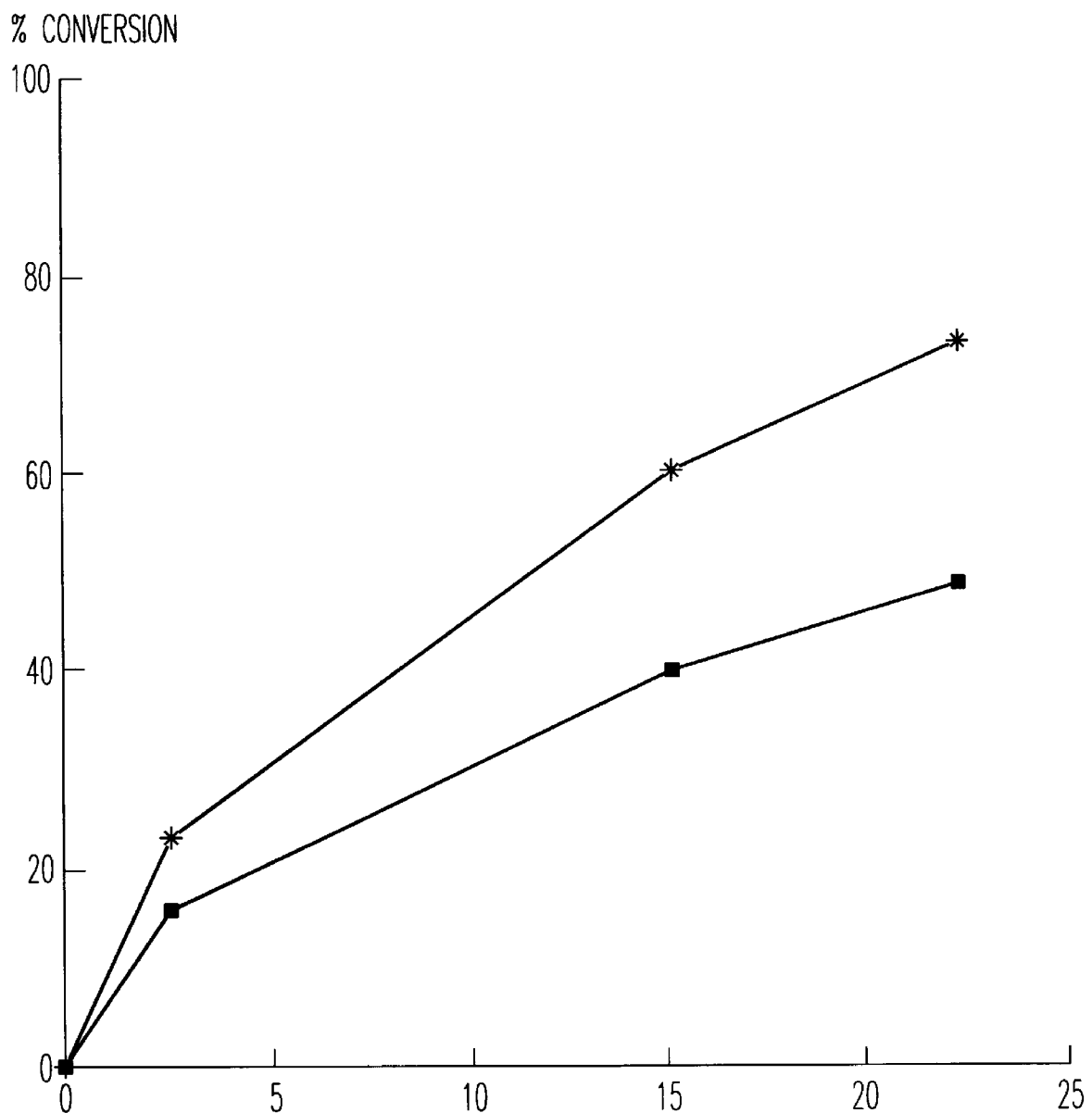

(A) line 1: soluble cellular fraction SMC305; line 2: insoluble cellular fraction SMC305; line 3: soluble cellular fraction SMC327; line 4: insoluble cellular fraction SMC327;

(B) line 1: soluble cellular fraction SMC305; line 2: insoluble cellular fraction SMC305; line 3: soluble cellular fraction SMC327; line 4: insoluble cellular fraction SMC327; FIG. 6: shows the conversion trend (%) of D,L-parahydroxy-phenylhydantoin over a period of time. In abscissa there is the time in hours and in the ordinate the conversion as a %: * indicates the strain *E.coli* SMC327 and ■ the strain *E.coli* SMC305.

Figure 4:
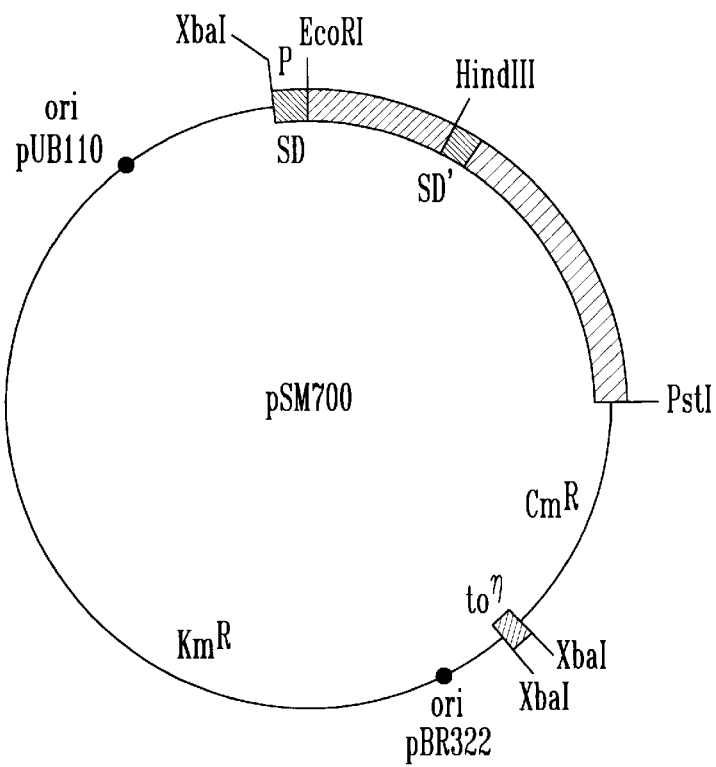
FIG. 4: Restriction map of the plasmid pSM700 containing the carbamoylase-hydantoinase operon, where P is the promoter and SD' is the modified Shine-Dalgarno upstream of the hydantoinase gene.

The plasmid pSM700, with the restriction map in FIG. 4, can be obtained using general known techniques starting from the plasmid pSM 651 CBS 203.94 inverting in the operon which encodes the enzymatic system the arrangement of the carbamoylase and hydantoinase genes and substituting the region containing the SD upstream of the hydantoinase gene with a region having the sequence:(SEQ ID NO:D

5' AAGGAGGAAA AATAT 3'

In particular, pSM700 was prepared with a method which comprises:

a) digesting the plasmid pSM651 with restriction enzymes HindIII and EcoRI;

b) ligating the plasmid DNA obtained in a) in the presence of T4 DNa ligase to obtain a plasmid pSM638 comprising the hydantoinase gene alone;

c) synthesizing two complementary oligonucleotides which contain the SD, the codons which encode the first two amino acids of hydantoinase and two sites (EcoRV and PstI) which allow the hydantoinase gene to be inserted immediately downstream of SD;

d) favouring the annealing of the two complementary oligonucleotides (linker);

e) ligating the linker obtained in d) with the plasmid pSM637 containing the carbamoylase gene alone digested with the enzymes HindIII and PstI to obtain an intermediate plasmid in which the linker is correctly inserted downstream of the carbamoylase gene;

f) isolating from the plasmid pSM638 an EcoRV-PstI fragment corresponding to the hydantoinase gene without the codons which encode the first two N-terminal amino acids;

g) ligating the fragment obtained in f) with the intermediate plasmid as in e) digested with EcoRV and PstI;

h) isolating the plasmid pSM700.

The plasmid pSM700 is then used for transforming host cells of a microorganism selected from *Escherichia coli* and *Bacillus subtilis* made competent with the conventional methods.

The enzymatic system of the present invention can be obtained by culturing the strains *E.coli* or *B.subtilis* transformed with the plasmid pSM700, under aerobic conditions, in an aqueous medium containing assimilable sources of carbon and nitrogen as well as various cations, anions and, optionally, traces of vitamins, such as biotin, thiamine, or amino acids.

Assimilable carbon sources comprise carbohydrates such as glucose, hydrolyzed starches, molasses, sucrose or other conventional carbon sources.

Examples of nitrogen sources can be selected, for example, from mineral ammonium salts, such as ammonium nitrate, ammonium sulphate, ammonium chloride or ammonium carbonate and urea or materials containing organic or inorganic nitrogen such as peptone, yeast extract or meat extract.

The following cations and anions are equally suitable for the object of the present invention: potassium, sodium, magnesium, iron, calcium, acid phosphates, sulphates, chlorides, manganese, and nitrates.

The fermentation is carried out, under stirring, at a temperature of between 25° and 28° C, preferably between 23° C. and 26° and at a pH of between 6 and 7.5, preferably between 6.5 and 7.0.

Operating under the preferred conditions specified above the carbamoylase and hydantoinase enzymes are obtained in high yields and in an almost completely soluble form.

The cells (biomass) recovered from the culture medium by means of the conventional techniques such as centrifugation or filtration are used in the conversion phase of the racemic mixtures of 5-substituted hydantoins.

Alternatively, the conversion reaction can be carried out using either the cellular extract obtained from the disintegration of the cells by sonication or French-Press, or enzymes purified or partially purified with the conventional methods, or enzymes immobilized on insoluble supports.

Numerous hydantoins substituted in position 5 can be used in the process of the present invention. Possible substituents in position 5 are selected from a linear or branched alkyl group with a number of carbon atoms of between 1 and 6, which can be mono or polysubstituted with hydroxy, carboxy, hydrosulphide or aminic groups or a phenyl or benzyl group which, in turn, can contain one or more substitutes in ortho, meta and para position. Examples of 5-substituted hydantoins are:

(D,L)-5-phenylhydantoin, (D,L)-5-; para-hydroxyphenyl hydantoin, (D,L)-5-methylhydantoin, (D,L)-5-isopropylhydantoin, (D,L)-5-thienylhydantoin, (D,L)-5-para-methoxyphenylhydantoin, (D,L)-5-parachloro phenylhydantoin, (D,L)-5-benzylhydantoin.

The conversion of the hydantoins into the corresponding D-α-amino acids is carried out in a nitrogen atmosphere in a hermetically closed apparatus, at a temperature of between 20° and 60° C, preferably between 30° and 45° C.

The pH of the reaction medium is maintained within values of between 6 and 10 and preferably between 7 and 8.5. This regulation of the pH can be carried out, for example, by adding a base aqueous solution such as an aqueous solution of ammonia, potassium hydroxide, sodium hydroxide, sodium or potassium carbonate.

The initial concentration of the hydantoins is generally between 2% and 30% by weight. As a result of the stereospecificity of the enzymes produced from the strains of the present invention, only the D-enantiomorphs of the hydantoins are hydrolyzed. As hydantoins however, spontaneously racemize more or less rapidly under the operating conditions, the L-enantiomorphs are completely converted into the corresponding D-α-amino acids.

The quantity of biomass which is added to the reaction mixture depends on the particular affinity of the substrate towards the enzymes. Generally a ratio by weight biomass/hydantoins of between 1/1 and 1/50 can be used.

The D-α-amino acids prepared with the process of the present invention can be recovered from the reaction medium with the conventional methods such as ionexchange chromatography or precipitation of the amino acid at its isoelectric point.

The plasmid pSM700 was deposited at the Bureau Voor Schimmelcultures, SK Baarn (Holland) as *E.coli* SMC327 where it received the deposit number CBS 668.95.

The following experimental examples provide a better illustration of the present invention but do not limit it in any way.

EXAMPLE 1
Construction of the plasmid pSM638

About 1.7 µg of the plasmid pSM651 CBS 203.94, containing the hydantoinase-carbamoylase operon, were digested with the restriction enzyme HindIII (4 units) (Boehringer) at 37° C. for 60 minutes and subsequently with EcoRI at 37° C. for 10 minutes. After blocking the enzymatic reaction at 65° C. for 10 minutes, the DNA was precipitated with 2.5 volumes of ethanol and resuspended in 12 µof buffer solution containing 0.05 mM of dNTPs (dATP, dGTP, dCTP, dTTP) and 1 U of Klenow polymerase (Boehringer) to make the ends blunt. The reaction was carried out at room temperature for 45 minutes.

The reaction mixture was then diluted to a final volume of 20 µl with a ligase buffer containing 1 mM ATP and 6% PEG 6000 and the plasmid DNA was ligated in the presence of 1 Unit of T4 DNA ligase at room temperature for about 4 hours. The mixture of ligases was used for transforming cells of E.coli 71/18 (BRL) made competent with 50 mM CaCl$_2$ (Dagert, M. and Ehrlich (1979), Gene, 6:23).

The transformants were selected on plates of LB medium (8 g/l Bactotryptone (DIFCO), 5 g/l NaCl, 15 g/l Agar (DIFCO), 0.5 g/l yeast extract) to which 20 µl/ml of chloramphenicol and 0.2 % 5-methyl hydantoin were added.

Figure 1:
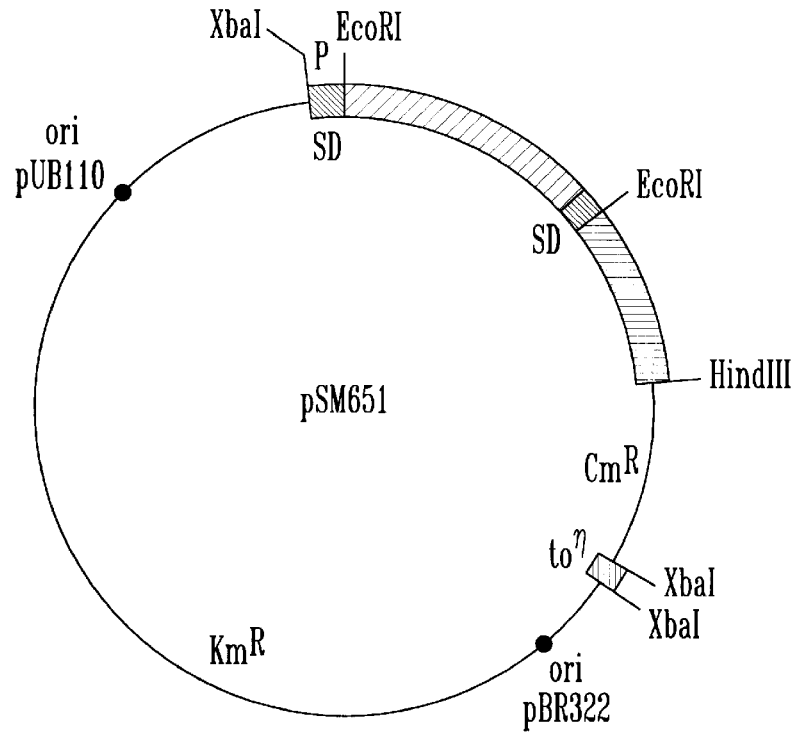
FIG. 1: Restriction map of the plasmid pSM651 containing the hydantoinase-carbamoylase operon, where P is the promoter and SD is the Shine-Dalgarno upstream of the genes.
Figure 2:
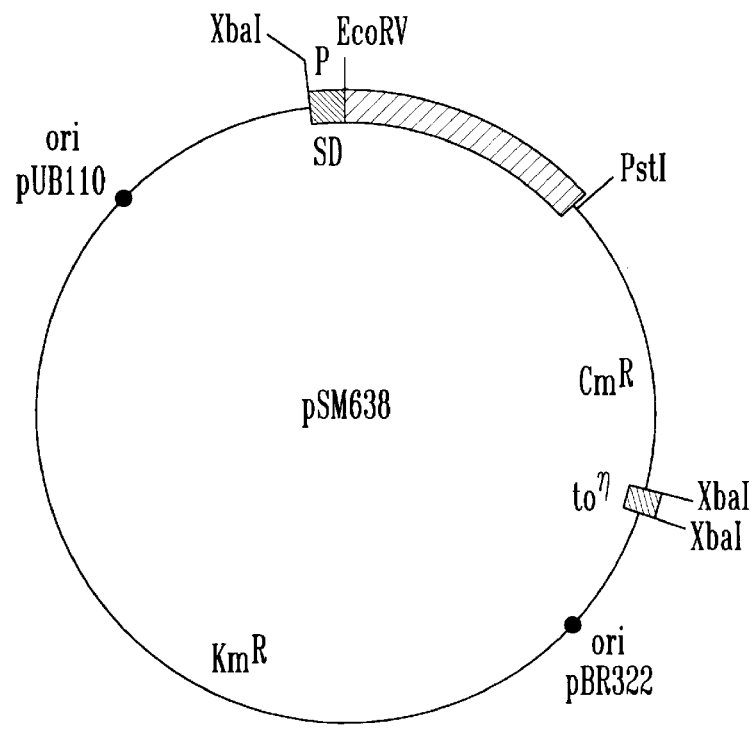
FIG. 2: Restriction map of the plasmid pSM638 containing the hydantoinase gene.
Figure 3:
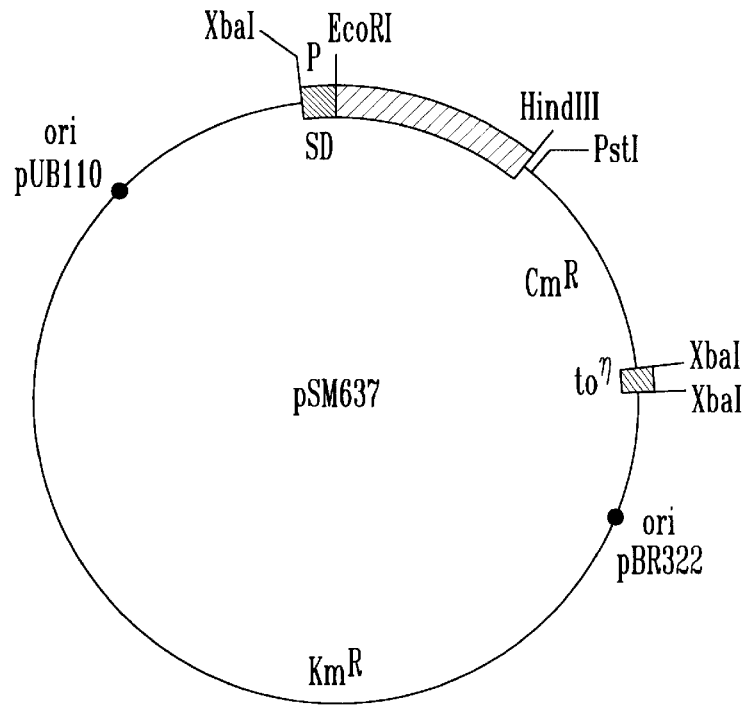
FIG. 3: Restriction map of the plasmid pSM637 containing the carbamoylase gene.

The plasmid DNA extracted from the positive clones was analyzed to verify the elimination of the carbamoylase gene and the presence of the hydantoinase gene alone. One of these plasmids was called pSM638 (FIG. 2), whereas the clone containing this plasmid SMC304.

Example 2
Construction of the plasmid pSM700

The following oligonucleotides (SEQ ID NO: 2 and 3) were synthesized, using a DNA Synthesizer One Plus (Beckmann):

HindIII EcoRV PstI
5'AG CTT AAG GAG GAA AAA TAT ATG GAT ATC CTG CA 3'
Met—3' A TTC CTC CTT TTT ATA TAC CTA TAG G 5'

These oligonucleotides contain an RBS (SD'), codons which encode the first two hydantoinase amino acids and two sites (EcoRV and PstI) which allow the hydantoinase gene to be inserted immediately after the RBS.

About 1.9 µg of these oligonucleotides were phosphorylated in 30 µl of solution containing 100 mM Tris-HCl pH 8.0 , 10 mM MgCl$_2$, 7 mM DTT, 1 mM ATP and 10 U of polynucleotide kinase (Promega) at 37° C. for 30 minutes. After inactivation of the kinase at 70° C. for 10 minutes, the solution was left to cool slowly to room temperature (20°–25° C.) for 30 minutes to favour the annealing between the two complementary strands.

At the same time 800 ng of the plasmid pSM637(Italian patent application MI94 A00726), containing the carbamoylase gene were digested with 2 U of the restriction enzymes HindIII and PstI at 37° C. for 1 hour. After checking that the digestion had taken place by charging an aliquot on agarose gel 0.8 %, the DNA was ligated with the linker.

In practice, 40 nm of the plasmid pSM637 digested as described above and 120 ng of the phosphorylated double strand linker were ligated in a ligase mixture in the presence of 1 U of T4 DNA ligase at 14° C. for 16 hours.

An aliquot (2 µl) of the ligase mixture thus obtained was used to transform cells of E.coli TG1 made competent with CaCl$_2$.

The transformants were subsequently selected on plates of LB medium (8 g/l Bactotryptone (DIFCO), 5 g/l NaCl, 15 g/l Agar (DIFCO), 0.5 g/l yeast extract) to which 20 µl/ml of chloramphenicol had been added.

The plasmid DNA extracted from the positive clones was analyzed by digestion with EcoRV and PstI to verify the exact insertion of the linker downstream of the carbamoylase gene. One of these plasmids was called pInt.

The plasmid pSM638 (2 µg) was digested with the enzymes EcoRv and PstI (4 U) and the EcoRV-PstI fragment of about 1380 bp, corresponding to the hydantoinase gene without the codons which encode the first two N-terminal amino acids, was purified by electrophoresis on agarose gel 0.8 % and subsequent extraction with Gelaset™.

This fragment (30 ng) and the intermediate plasmid pInt (about 50 ng), previously digested with the enzymes EcoRv and PstI, were ligated in 10 µl of ligase mixture in the presence of 1 U of T4 DNA ligase, at 16° C. for 16 hours.

The ligase mixture was used for transforming competent cells of E.coli 71/18. The transformants were subsequently selected on plates of LB medium (8 g/l Bactotryptone (DIFCO), 5 g/l NaCl, 15 g/l Agar (DIFCO), 0.5 g/l yeast extract) to which 20 µl/ml of chloramphenicol had been added. The plasmid DNA extracted from the positive clones was analyzed by digestion with EcoRV and PstI to verify the exact insertion of the hydantoinase gene downstream of the linker.

One of these plasmids contained the carbamoylasehydantoinase operon where the region immediately upstream of the two genes is the following:(SEQ ID NO :4 AND 5)

AAA GGA GGA ATT CTT ATC . . . Carbamoylase
AAG GAG G AA AAA TAT ATG . . . Hydantoinase This plasmid was called pSM700 and the clone which contains it SMC327.

EXAMPLE 3
Expression of the Carbamoylase-hydantoinase operon

A) Precultures from single colonies of the E.coli strains SMC305 and SMC327, containing the plasmids pSM651 and pSM700 respectively, were inoculated in two 50 ml flasks each containing 10 ml of LB medium to which 20 µg/ml of chloramphenicol had been added. The flasks were incubated, under stirring (220 rpm), at 37° C. and at 250° C. until an optical density of 4.0 determined at 600 nm (optical path 1 cm).

Aliquots (5 ml) of the culture broths were centrifugated at 16,000 rpm (4° C., for 1 minute) and the recovered cells were resuspended in 300 µl of 20 mM NaPO$_4$ buffer pH 8.0 containing 20 % glycerol and lysed by sonication (Soniprep150, MSE 1 minute pulses, at medium voltage). Aliquots (5 µof the two lysates were charged onto polyacrylamide gel.

Figures 5A, 5B:
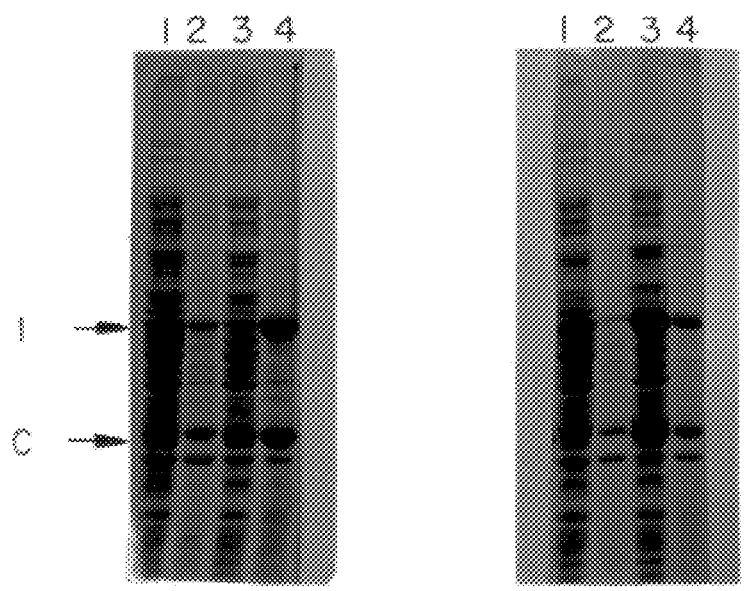
FIG. 5: Electrophoretic analysis of the hydantoinase and carbamoylase expression in the cellular extracts of SMC305 and SMC327 after growth at 37° C. (A) and at 25° C. (B) and where.

After coloring with Coomassie R-250 (Laemmli, Nature: 227, 680, 1970) two proteic bands were revealed with a molecular weight of 50,000 and 34,000 Daltons absent in the extract of the untransformed E.coli 71/18 strain. In addition, densitometric analysis carried out on the same gel colored with Coomassie showed that these proteins were expressed in E.coli SMC327 cultivated at 25° C. in higher quantities than E.coli SMC305 cultivated at 37° C. (FIG. 5).

B) Determination of the enzymatic activities

The determination of the hydantoinase activity was carried out at 40° C. in 3 ml of 0.2 M Na-P0$_4$ buffer pH 8.0 containing D,L-p-hydroxyphenyl hydantoin 20 mM. The content of carbamoyl at various reaction times was determined by removing 0.6 ml of reaction mixture which were immediately treated with 0.2 ml of trichloroacetic acid at 15% in water. The precipitated proteins were removed by centrifugation and 0.25 ml of Ehrlich reagent (10% 4-dimethylaminobenzaldehyde) were added to 0.5 ml of surnatant for the calorimetric determination at 438 nm of the carbamoyl formed. At the same time, the content of amino acid was calorimetrically determined at 625 nm on an aliquot (50 μl) of the reaction mixture using the Berthelot reagent according to the procedure of Weatherburn, M. W. (Anal. Chem., vol. 39, 971, 1967). The hydantoinase activity results from the sum of the quantity of carbamoyl and amino acid produced. The quantity of enzyme which hydrolyzes a micromole of hydantoin in one minute at 40° C. under the test conditions described above, is defined as the enzymatic unit.

The determination of the carbamoylase activity was carried out at 40° C. in 0.5 ml of Na-P0$_4$ 0.2 M buffer pH 7.0 containing D-carbamoyl-p-hydroxyphenyl glycine 0.12 M. The content of amino acid was determined at various reaction times by removing 50 μl of the reaction mixture and operating as described above. The quantity of enzyme which hydrolyzes a micromole of carbamoyl in one minute at 40° C. under the test conditions described above, is defined as the enzymatic unit. The results are shown in table 1 below.

TABLE 1

| Strain E. coli | Growth temp. (°C.) | Carbamoylase (U/ml) | Hydantoinase (U/ml) |
|---|---|---|---|
| SMC305 | 37 | 1.29 | 0.29 |
| SMC327 | 37 | 1.75 | 0.07 |
| SMC305 | 25 | 0.41 | 0.08 |
| SMC327 | 25 | 2.04 | 0.25 |

These results show that the strain *E.coli*327 grown at 25° C. has a greater content of carbamoylase and hydantoinase activity than the strain grown at 37° C. In addition, the strain *E.coli*327 has a greater content of carbamoylase activity than the strain *E.coli*305 grown at both 37° C. and 25° C.

EXAMPLE 4
Conversion of (D.L)-para-hydroxy-phenylhydantoin to D-para-hydroxy-phenylglycine The productivity of the biomass was examined at 40° C. under a nitrogen atmosphere, to prevent oxidation, using 15 ml reactors stirred by a magnetic anchor and closed with rubber tops.

Each reactor contained 80 mg of humid biomass and 10 ml of a suspension at 8% of (D,L)-para-hydroxyphenylhydantoin in a buffer of NaPO4 0.2 M, pH 8.0.

After 2.5, 15 and 22 hours aliquots of the reaction mixtures were removed, diluted in an aqueous solution containing 5% of acetonitrile and 0.01% of phosphoric acid and centrifuged at 16,000 rpm for 10 minutes, to remove the turbidity present.

The samples thus prepared were analyzed at HPLC to determine the concentration of the para-hydroxy-phenylglycine and N-carbamoyl-para-hydroxy-phenylglycine.

For this purpose a 4.6×250 mm Ultrasphere ODS Beckman column was used operating under isocratic conditions at a flow of 1/ml minute and monitoring the eluate at 272 nm. The same aqueous solution used for the dilution of the samples was used as mobile phase.

Table 2 shows the formation kinetics of the carbamyl and amino acid.

TABLE 2

| | SMC305 (37° C.) | | SMC327 (25° C.) | |
|---|---|---|---|---|
| Time (hrs) | p-OH-phenyl-glycine (mmol/ml) | N-carbamoyl phenyl-glycine (mmol/ml) | p-OH-phenyl-glycine (mmol/ml) | N-carbamoyl phenyl-glycine (mmol/ml) |
| 2.5 | 28 | 39 | 57 | 40 |
| 15 | 119 | 48 | 203 | 49 |
| 22 | 153 | 51 | 255 | 53 |

From the results it can be observed that, with the same biomass and reaction time, the accumulation of amino acid is higher if the strain *E.coli* SMC327 is used.

FIG. 6 shows the conversion data, with respect to the starting hydantoin, obtained by adding the amino acid and carbamoyl present at different times in the reaction mixture.

We claim:

1. An improved process for the preparation of D-α-amino acids by the stereoselective conversion at a temperature of 20°–60° C. of racemic mixtures of 5-substituted hydantoins with an enzymatic system produced by a microorganism, wherein said microorganism is obtained by:
    (a) construction of the plasmid pSM700 CBS 668.95 comprising the carbamoylase-hydantoinase operon under the control of a constitutive promoter and where the region comprising the RBS upstream of the hydantoinase gene has the sequence AAGGAGGAAA AATAT; (b) transformation of a microorganism with the plasmid pSM700; and (c) fermentation of the transformed microorganism in an aqueous medium containing assimilable sources of carbon and nitrogen, cations, anions and, optionally, vitamins, under aerobic conditions, at a temperature of between 20° and 28° C.

2. The process according to claim 1, characterized in that the microorganism is selected from *Escherichia coli* and *Bacillus subtilis*.

3. The process according to claim 1, characterized in that the microorganism is cultivated at a temperature of between 23° and 26° C.

4. The process according to claim 1, wherein assimilable carbon sources comprise carbohydrates like glucose, hydrolyzed starches, molasses, sucrose.

5. The process according to claim 1, characterized in that nitrogen sources can be selected from mineral ammonium salts, such as ammonium nitrate, ammonium sulphate, ammonium chloride or ammonium carbonate and urea or materials containing organic or inorganic nitrogen such as peptone, yeast extract or meat extract.

6. The process according to claim 1, characterized in that the cations and anions are selected from potassium, sodium, magnesium, iron, calcium, acid phosphates, sulphates, chlorides, manganese, and nitrates.

7. The process according to claim 1, characterized in that the 5-substituted hydantoin is selected from (D,L)-5-phenylhydantoin, (D,L)-5-para-hydroxyphenylhydantoin, (D,L)-5-methylhydantoin, (D,L)-5-isopropylhydantoin, (D,L)-5-thienylhydantoin, (D,L)-5-para-methoxyphenylhydantoin, (D,L)-5-parachlorophenylhydantoin, (D,L)-5-benzylhydantoin.

8. The process according to claim 7, characterized in that the hydantoin is (D,L)-5-para-hydroxyphenylhydantoin.

9. The process according to claim 7, characterized in that the hydantoin is (D,L)-5-phenylhydantoin.

10. The process according to claim 1, characterized in that the temperature is between 30° and 45° C.

11. The process according to claim 1, characterized in that the conversion reaction is carried out at a pH of between 6.0 and 10.

12. The process according to claim 11, characterized in that the pH is between 7.0 and 8.5.

13. The process according to claim 1, characterized in that the conversion reaction is carried out using a weight ratio humid biomass/hydantoin of between 1/1 and 1/50.

14. The plasmid pSM700 deposited at the Bureau Voor Schimmelcultures, SK Baarn (Holland) where it received the deposit number CBS 668.95.

15. A microorganism selected from *Bacillus subtilis* and *Escherichia coli* transformed with the plasmid pSM700.

16. The microorganism of claim 15, *Escherichia coli* SMC327 CBS 668.95.

* * * * *